(12) United States Patent
Werneth et al.

(10) Patent No.: US 9,962,275 B2
(45) Date of Patent: May 8, 2018

(54) TEMPORARY GASTRIC DEVICE (TGD) AND METHOD OF USE

(76) Inventors: Randy Louis Werneth, San Diego, CA (US); Kaushik Aroonkumar Patel, Poway, CA (US)

(*) Notice: Subject to any disclaimer, the term of this patent is extended or adjusted under 35 U.S.C. 154(b) by 230 days.

(21) Appl. No.: 12/900,093

(22) Filed: Oct. 7, 2010

(65) Prior Publication Data
US 2012/0089169 A1 Apr. 12, 2012

(51) Int. Cl.
*A61M 29/00* (2006.01)
*A61F 5/00* (2006.01)

(52) U.S. Cl.
CPC ............ *A61F 5/0036* (2013.01); *A61F 5/003* (2013.01)

(58) Field of Classification Search
CPC ...... A61F 5/003; A61F 5/0033; A61F 5/0036; A61F 5/0043
USPC ........ 606/192, 191, 195, 157, 194; 128/899; 604/96.01, 97.01, 101.01, 287, 288; 424/428; 446/220, 221; 29/527.1
See application file for complete search history.

(56) References Cited

U.S. PATENT DOCUMENTS

| | | |
|---|---|---|
| 3,551,556 A | 5/1970 | Kliment et al. |
| 3,944,064 A | 3/1976 | Bashaw et al. |
| 4,178,361 A | 12/1979 | Cohen et al. |
| 4,501,264 A | 2/1985 | Rockey |
| 4,641,653 A | 2/1987 | Rockey |
| 4,739,758 A | 4/1988 | Lai et al. |
| 4,763,653 A | 8/1988 | Rockey |
| 4,812,315 A | 3/1989 | Tarabishi |
| 5,049,106 A | 9/1991 | Kim et al. |
| 5,129,915 A | 7/1992 | Cantenys |
| 5,336,486 A | 8/1994 | Acharya |
| 5,750,585 A | 5/1998 | Park et al. |
| 6,160,084 A | 12/2000 | Langer et al. |
| 6,245,103 B1 * | 6/2001 | Stinson ............. A61F 2/90 606/200 |
| 6,271,278 B1 | 8/2001 | Park et al. |
| 6,375,668 B1 * | 4/2002 | Gifford et al. ............ 606/200 |
| 6,388,043 B1 | 5/2002 | Langer et al. |
| 6,488,962 B1 | 12/2002 | Berner et al. |
| 6,579,301 B1 | 6/2003 | Bales et al. |
| 6,585,748 B1 * | 7/2003 | Jeffree ........................ 606/200 |
| 6,627,206 B2 | 9/2003 | Lloyd |
| 6,733,512 B2 | 5/2004 | McGhan |
| 6,746,460 B2 | 6/2004 | Gannoe et al. |
| 6,833,488 B2 | 12/2004 | Bucevschi et al. |
| 6,981,980 B2 | 1/2006 | Sampson et al. |
| 6,994,095 B2 | 2/2006 | Burnett |
| 7,033,373 B2 | 4/2006 | de la Torre et al. |
| 7,056,305 B2 | 6/2006 | Garza Alvarez |
| 7,112,186 B2 | 9/2006 | Shah |

(Continued)

FOREIGN PATENT DOCUMENTS

| | | |
|---|---|---|
| WO | 2005084724 | 9/2005 |
| WO | 2007115169 | 10/2007 |
| WO | 2009049105 | 4/2009 |

*Primary Examiner* — Jonathan Miles
*Assistant Examiner* — Mohamed Gabr
(74) *Attorney, Agent, or Firm* — Michael R Shevlin (57) ABSTRACT

A gastric device for a stomach having a pyloric valve comprising a first volume filling agent disposable within the stomach and transitionable from a first displacement to a second displacement larger than the first displacement, and wherein the first volume filling agent does not pass through the pyloric valve in the normal digestive process.

10 Claims, 7 Drawing Sheets

(56) References Cited

U.S. PATENT DOCUMENTS

| | | | |
|---|---|---|---|
| 7,172,613 B2 | 2/2007 | Wazne | |
| 7,223,277 B2 | 5/2007 | DeLegge | |
| 2005/0228504 A1* | 10/2005 | Demarais | 623/23.65 |
| 2006/0058829 A1 | 3/2006 | Sampson et al. | |
| 2006/0142794 A1 | 6/2006 | Lendlein et al. | |
| 2007/0135831 A1 | 6/2007 | Burnett | |
| 2007/0178160 A1 | 8/2007 | Burnett | |
| 2007/0276428 A1* | 11/2007 | Haller | A61F 5/0003 606/192 |
| 2008/0109027 A1* | 5/2008 | Chen et al. | 606/191 |
| 2008/0241094 A1 | 10/2008 | Burnett et al. | |
| 2008/0249635 A1* | 10/2008 | Weitzner | A61F 5/0003 623/23.65 |
| 2008/0300618 A1 | 12/2008 | Gertner | |
| 2008/0306506 A1 | 12/2008 | Leatherman | |
| 2009/0093838 A1* | 4/2009 | Paganon | 606/192 |
| 2009/0192535 A1 | 7/2009 | Kasic, II | |
| 2009/0259246 A1 | 10/2009 | Eskaros et al. | |
| 2010/0076481 A1* | 3/2010 | Stephens et al. | 606/192 |
| 2010/0100117 A1* | 4/2010 | Brister | A61F 5/003 606/192 |
| 2010/0137897 A1* | 6/2010 | Brister et al. | 606/192 |

* cited by examiner

TEMPORARY GASTRIC DEVICE (TGD) AND METHOD OF USE

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a device for treating obesity.

BACKGROUND OF THE INVENTION

Obesity is a condition defined by having an excessive amount of body fat. As of 2006, there are an estimated 70 million obese people in the United States. By some estimates, there are 1 billion obese individuals worldwide. In addition, hospital costs associated with childhood obesity have risen from about $35 million in 1979 to $127 million in 1999. Obesity not only affects the quality of life and productivity of those effected, it has also been proven to lead to long-term health related complications, such as diabetes, heart disease, hypertension, cancer, and a myriad of gastrointestinal maladies. Some researchers estimate that if the obesity epidemic is not brought under control, the number of adults with type II diabetes could skyrocket in the next decade.

Surgical treatments, for example, stomach stapling and bypass operations, are methods for inducing substantial weight loss in obese people. The mechanism behind the success of these surgical treatments is unclear because obesity is such a complex condition. Some researchers propose that surgery does no more than provide biofeedback for appetite retraining. Other researchers maintain that surgery alters the physiology of the patient such that satiety is induced earlier or fewer nutrients are absorbed. Regardless, the consensus among most obesity researchers is that at the current time, long-term weight loss is achievable by surgical means and that the success of surgery is due to a myriad of biological changes.

However, despite the efficacy of surgical procedures, they remain highly invasive and carry significant morbidity, including ubiquitous surgical complications such as infection, high incidence of pulmonary morbidity such as pneumonia and pulmonary embolism, and risk of leakage at the surgical site, which can result in a spectrum of consequences ranging from an extended hospital stay to death. Furthermore, surgery is a poor option for adolescents in whom the long-term consequence of malabsorption of nutrients is not known. In addition, many patients resist such irreversible, life altering procedures.

Dietary supplements have also been used to impart of feeling of satiety, to slow gastric transit of nutrients within a patient, and to reduce the impulse to eat. For example, fiber supplements may be ingested orally and swell within a patient's stomach to promote a temporary feeling of fullness. However, fiber supplements only remain within the stomach for a short period of time, and therefore do not provided a sustained feeling of satiety that fully promotes weight loss. Also, the gastrointestinal side effects of ingesting fiber supplements can be severe. For example, the more the fiber consumed by a patient, the greater the chance that the fiber will cause bloating, abdominal pain, and diarrhea. As such, only a small volume of fiber may be consumed at any one time, limiting its efficacy. Moreover, in order to obtain any benefit from fiber supplements, they need to be taken at least once a day, typically prior to a meal, for many days, thus creating a risk that patients may forget to ingest them or ingest too many.

Alternatively, recent attempts have been made to use an intragastric balloon to displace volume within the stomach such that a smaller volume of food leads to an earlier feeling of satiety. Currently, intragastric balloons on the market can lead to complications such as obstruction and mucosal erosion. Additionally, the incidence of nausea, vomiting, and epigastric pain may be present owing to the balloon having a tendency to obstruct the passage of food out of the stomach. This obstructive tendency is due in part because current intragastric balloon devices are filled with saline, which acts as ballast, and causes the balloon to sink to the bottom of the stomach and obstruct the pylorus.

Accordingly, what is needed is a temporary gastric device that is minimally invasive, avoids obstructing the passage of food out of the stomach, and achieves effective results.

SUMMARY OF THE INVENTION

The present invention advantageously provides for a temporary gastric device comprising a biodegradable ingestible delivery structure. A first volume filling agent retained by the delivery structure transitionable from a first state to a second state and defining suitable properties to remain within a human stomach for at least 30-180 days is also included.

In another embodiment, the device includes a biodegradable ingestable capsule and first volume filling agent disposed within the capsule. A composition disposed within the first volume filling agent is included, the composition producing a gas operable to expand the first volume filling agent such that it does not pass through the pyloric valve in the normal digestive process.

In yet another embodiment, the device includes a biodegradable and impermeable ingestible delivery structure and a biodegradable balloon disposed within the capsule. A coiled shape memory biodegradable polymer disposed within the balloon being operable to expand the biodegradable balloon is also included, the biodegradable balloon and the coiled shape memory biodegradable polymer being expandable to a size larger than the diameter of the pyloric canal and the diameter of the esophagus.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
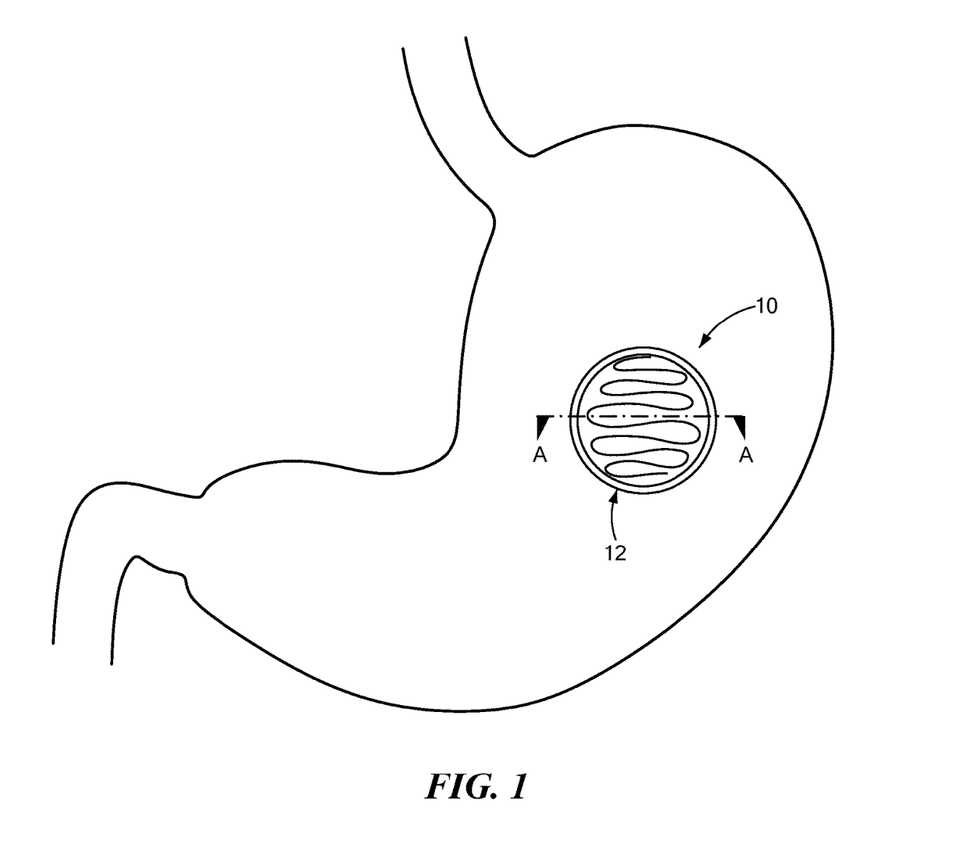
FIG. 1 is a perspective view of an exemplary temporary gastric device disposed within a stomach.
Figure 1A:
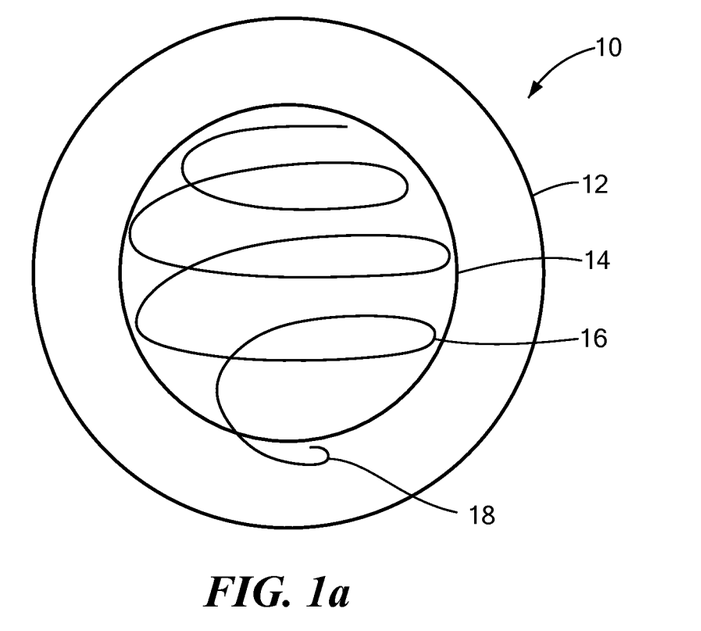
FIG. 1a is a cross-sectional view of the exemplary temporary gastric device along slice A-A shown in FIG. 1.

Now referring to the drawings where like reference designators refer to like elements, there is shown in FIGS. 1 and 1A an exemplary embodiment of a temporary gastric device in accordance with the principles of the present invention and designated generally as "10." The device 10 includes a delivery structure 12 sized to house the components of the invention. The delivery structure 12 may be a biodegradable material such as a gelatin capsule that may be swallowed and ingested by a patient. For example, the delivery structure 12 may be a size 13, or any sized, gelatin capsule that disintegrates upon exposure to stomach fluid. Further, the delivery structure 12 may have sufficient lubricity and resistant to digestive enzymes and acids, such that the delivery structure is resistant to erosion until such time is it contacts stomach fluids.

Referring now to FIG. 1a, retained within or by the delivery structure 12 is a first volume filling agent 14 that is transitionable from a first displacement to a second displacement larger than the first displacement. As used herein, the term "displacement" refers to the amount of space in the stomach (between about 200 to 500 cc), for example the first volume filling agent, occupies within a volume, for example the stomach.

The first volume filling agent 14 may be a flexible self-contained structure, such as a balloon, that is generally resistant to disintegration from stomach acid for a period of time. For example, the first volume filling agent 14 may be a thin-walled medical grade balloon composed of FEP/PI/FEP (Fluorinated ethylene propylene/polymide/fluorinated ethylene propylene) or other polymers, and may further be thermoplastic, such that it is pliable when heated, without any change to its inherent properties. In an embodiment where the first volume filling agent 14 is balloon, the balloon may define a rigid volume or a flexible volume depending on the desired size of the balloon. The first volume filling agent 14 may further be gas permeable or substantially impermeable. The permeability of the first volume filling agent 14 may be variable depending on the size of the molecules or polymers desired to be contained within the first volume filling agent 14. For example, the first volume filling agent 14 may be gas permeable such that gaseous particles may diffuse in, but larger particles, such as polymers and gels, may be trapped inside.

The first volume filling agent 14 may further be biodegradable and have a lubricious coating on its outer surface so as to not stick to the walls of the stomach. Alternatively, the surface of the second volume filling agent 14 may be coated with a pharmaceutical or antimicrobial agent, such that the pharmaceutical or antimicrobial agent may be eluded from the surface of the first volume filling agent 14 for a predetermined time period. The first volume filling agent 14 may be composed of a material that degrades after a predetermined amount of time, for example, 180 days. The first volume filling agent 14 may define properties as discussed above such that it remains within the human stomach for at least 30 days and such that it degrades naturally over time or in response to a solvent, acid, or other chemical that may be ingested following the predetermined amount of time. After the predetermined amount of time, the first volume filling agent 14 may degrade and pass through the digestive system, eliminating the need to remove the device 10 from the body by invasive means.

Continuing to refer to FIG. 1A, disposed within or retained by the first volume filling agent 14 may a biocompatible second volume filling agent 16 also transitionable from a first displacement to a second displacement larger than the first displacement. For example, as shown in FIG. 1A, the second volume filling agent 16 may be a superelastic and/or shape memory material, such as Nitinol or Nafion, or any material that after heating and deformation resumes its original shape when reheated. The second volume filling agent 16 may further be expandable to a variety of shapes in response to variable temperatures. For example, the second volume filling agent 16 may expand linearly as the temperature increases or may change shapes depending on the temperature. Alternatively, the second volume filling agent 16 may unfold or decompress to a previously determined bias shape as the first volume filling agent 14 expands or the delivery structure 12 degrades. In an exemplary embodiment, the second volume filling agent 16 expands when its temperature reaches 35° C. Alternatively, the second volume filling agent 16 may be composed of nitinol wire only; stainless steel; a combination of Nitinol and a shape memory polymer, such as Nafion; a shape memory polymer only; a hydrogel; or a balloon-type structure with similar suitable properties to that of the first volume filling agent 14, depending on the desired action of the second volume filling agent 16.

In an exemplary operation, the second volume filling agent 16 expands or unfolds when disposed within the stomach of the patient, which in turn applies pressure to the first volume filling agent 14 causing its expansion. Further, the second volume filling agent 16 may expand or unfold to a particular size such that it does not become lodged within any section of the stomach or the esophagus, while providing a feeling of satiety to the patient. For example, the second volume filling agent 16 may expand to occupy a space within the stomach of about 200 cc to about 500 cc. Similar to the first volume filling agent 14, the second volume filling agent 16 may be biodegradable after a predetermined amount of time to allow passage of the device 10. For example, the second volume filling agent 16 may be composed of a biodegradable and biocompatible shape memory polymer, hydrogel, or a biodegradable balloon composed of copolymers, for example, polyketal or PLGA. Accordingly, the second volume filling agent 16 may degrade upon exposure to stomach acid soon after the first volume filling agent 14 degrades.

The shape of the second volume filling agent 16 may also be variable and may further be fabricated such that when expanded, it is biased in a particular configuration. For example, as shown in FIG. 1A, in an embodiment where the second volume filling agent 16 is a wire, the second volume filling agent 16 may expand to form a substantially coiled structure or define a stent-like structure. Alternatively, the second volume filling agent 16 may define a substantially symmetric spherical coil such that the center of the spherical coil has the largest diameter and each end portion of the spherical coil has the smallest diameter. The delivery structure 12 may operate to compress the second volume filling agent 16, such that when the delivery structure 12 degrades the second volume filling agent 16 may expand to its fabricated biased state.

Alternatively, the second volume filling agent 16 may be composed of an electroactive polymer such that it can be expanded and/or contracted remotely. For example, the second volume filling agent 16 may include sensors or actuators (not shown) that may respond to an applied electric field, magnetic or electromagnetic, to adjust the size of the second volume filling agent 16. As such, it is contemplated that the second volume filling agent 16 may be re-sized overtime for adjustment and for removal. Optionally, the second volume filling agent 16 may include or be composed of an electro-active polymer (EAP) that may be actuated to release a chemical that degrades the second volume filling agent 16, such that it may be passed through the digestive system. It is further contemplated that the second volume filling agent 16 may define any shape or size and that the first volume filling agent 14 may accommodate any expansion of the second volume filling agent 16. For example, the first volume filling agent 14 and the second volume filling agent 16 may be expandable to a size larger than the diameter of the pyloric valve and the diameter of the esophagus to prevent the device 10 from causing an undesirable occlusion.

Figure 2:
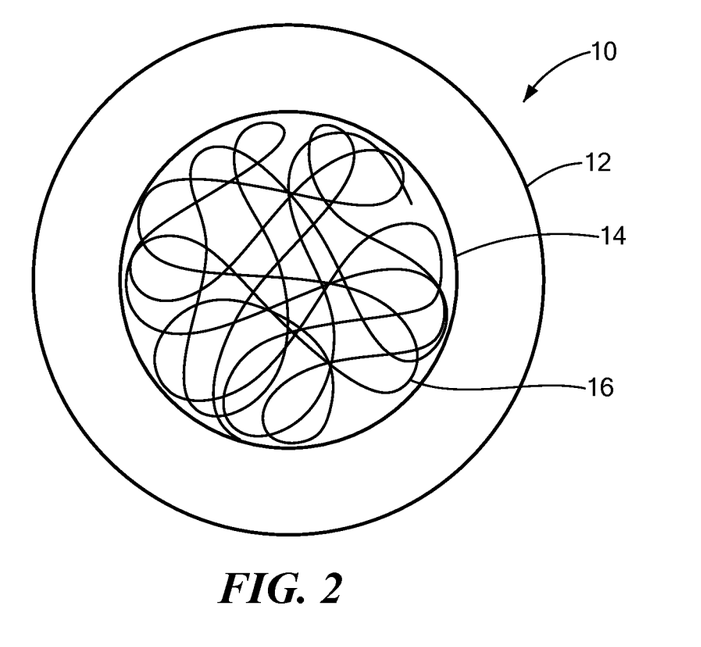
FIG. 2 is a cross-sectional view of another embodiment a temporary gastric device along slice A-A shown in FIG. 1.

Referring now to FIG. 2, in another embodiment the second volume filling agent 16 is a hydrogel that may expand to form any number of shapes, including an amorphous structure. In such a configuration, the first volume filling agent 14 may be generally permeable to water and/or gastric fluids, but impermeable to the hydrogel, such that it remains contained within the first volume filling agent 14. Alternatively, the first volume filling agent 14 may act as a filter to allow only water to penetrate within. For example, after the delivery structure 12 erodes in the stomach, water may diffuse into the first volume filling agent 14 and cause the second volume filling agent 16 to swell and expand the first volume filling agent 14. To facilitate the expansion of the hydrogel, water may be consumed contemporaneously with the device 10. In another embodiment, the first volume filling agent 14 is a hydrogel and upon disintegration of the delivery structure 12, the first volume filling agent 14 may swell in response to water or gastric fluids to a predetermined size.

The second volume filling agent 16 may also be fabricated such that it defines a first engagement element 18 (FIG. 1a) extending from either or both ends of the second expandable element 16. The first engagement element 18 may be curved to facilitate the removal of the device 10 with an endoscope or other esophageal device should it be necessary. In an exemplary embodiment, the first engagement element 18 may extend and span through the first volume filling agent so that it may be retrieved without affecting the properties of the first volume filling agent 14.

Figure 3:
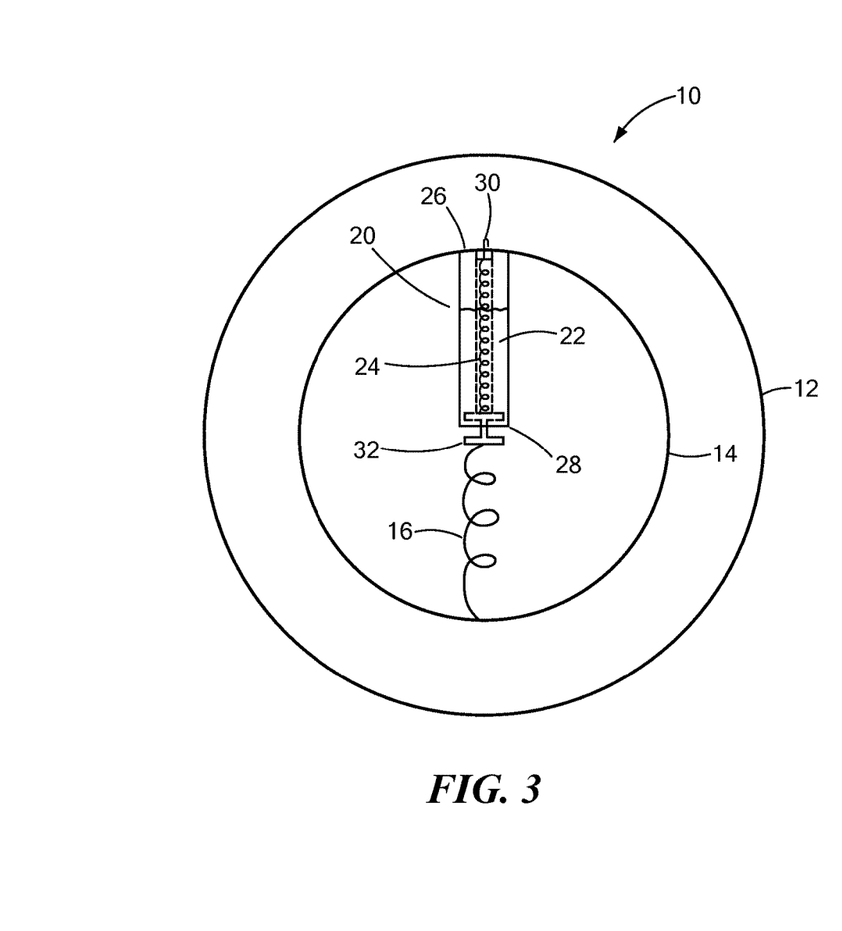
FIG. 3 is a cross-sectional view of another embodiment a temporary gastric device along slice A-A shown in FIG. 1.

Referring now to FIG. 3, the device 10 may further include a pouch 20 at least partially disposed within the first volume filling agent 14. The pouch 20 may be composed of biodegradable and biocompatible materials, such as a medical grade balloon or an elastomeric material, and may be glued within or otherwise affixed to the first volume filling agent 14. In the embodiment shown in FIG. 3, the pouch 20 defines a substantially cylindrical shape within the first volume filling agent 14, but may define any shape or size. The pouch 20 may further be flexible or substantially inflexible.

The pouch 20 may further be gas-impermeable or semi-impermeable, allowing some gaseous particles to diffuse. The pouch 20 may be filled with a gas, such as $CO_2$ or $N_2$, which may be pressurized or unpressurized. The $CO_2$ may be created within the pouch 20 by, for example, mixing one or more compositions 22 comprising: sodium bicarbonate with citric acid and water; sodium bicarbonate with water and heat; sodium bicarbonate with a citric acid solution; and/or a combination thereof. For example, prior to swallowing the device 10, the pouch 20 may be injected with a solution of any of the above compositions 22. The composition 22 may begin to react when disposed within the stomach, owing to the increased temperature in the stomach. As the compositions 22 react they produce gaseous particles, such as $CO_2$ that expand to fill the pouch 20 and applies pressure to the pouch 20.

Continuing to refer to FIG. 3, the pouch 20 may further include a piercing element 24, for example a needle, extending from a first portion 26 of the pouch 20 to a second portion 28 of the pouch 20. The piercing element 24 may be a biodegradable and biocompatible material, for example, an expandable polymer, thermoplastic material, or an electroactive polymer as discussed above, for example, a piezoelectric ceramic that exhibits a change in size or shape when stimulated by an electric field, magnetic or electromagnetic, or that may release a chemical that degrades particular structures. In the embodiment shown in FIG. 3, the piercing element 24 is a shape-memory polymer defining a coiled needle-like structure. The piercing element 24 may further define a second engagement element 30, for example a hook, extending from the second portion 28 of the pouch 20. The second engagement element 30 operates similar to the first engagement element 18 to facilitate the removal of the device 10.

The pouch 20 may further include a separation element 32 at least partially disposed within and partially surrounding the first portion 26 of the pouch 20. For example, as shown in FIG. 3, the separation element 32 may be substantially I-shaped, such that the a portion of the separation element 32 is disposed within the pouch 20, a portion of the separation element 32 is disposed outside the pouch, and a portion of the separation element 32 defines a part of the perimeter the pouch 20. The separation element 32 may be a gas permeably or gas impermeable membrane. The second volume filling agent 16 may optionally be affixed to a portion of the separation element 32 extending from an end portion of the separation element towards the first volume filling agent 14.

Figure 4:
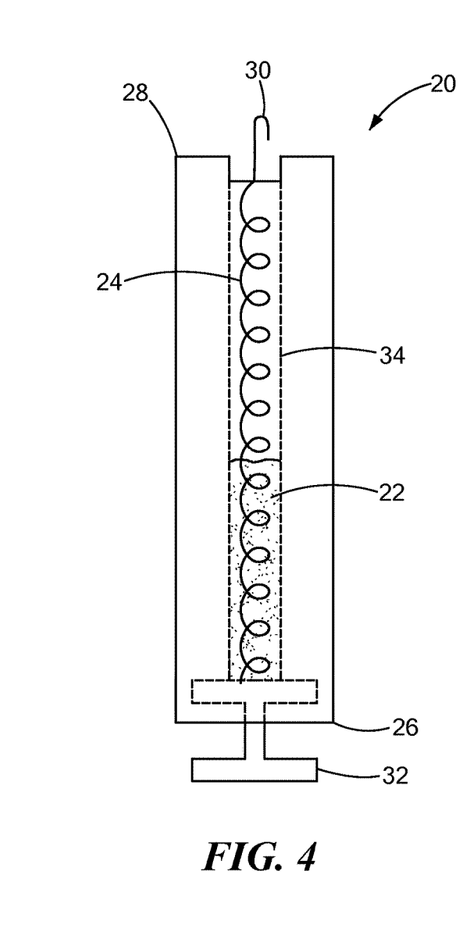
FIG. 4 is a cross-sectional view the pouch shown in FIG. 3.

Referring now to FIG. 4, the pouch 20 may further include a tube 34 extending from the first portion 26 to the second portion 28 of the pouch. The tube 34 may be gas impermeable or semi impermeable such that gaseous particles such as $CO_2$ or $N_2$ may diffuse out of the tube 34 but liquids remains trapped inside the tube. The piercing element 24 may be disposed within the tube 34, which may be positioned such that when expanded it contacts and pierces the separation element 32. The tube 34 may be flexible such that it may expand to apply pressure to the pouch 20 and further expand to fill the first volume filling agent 14.

Figure 5:
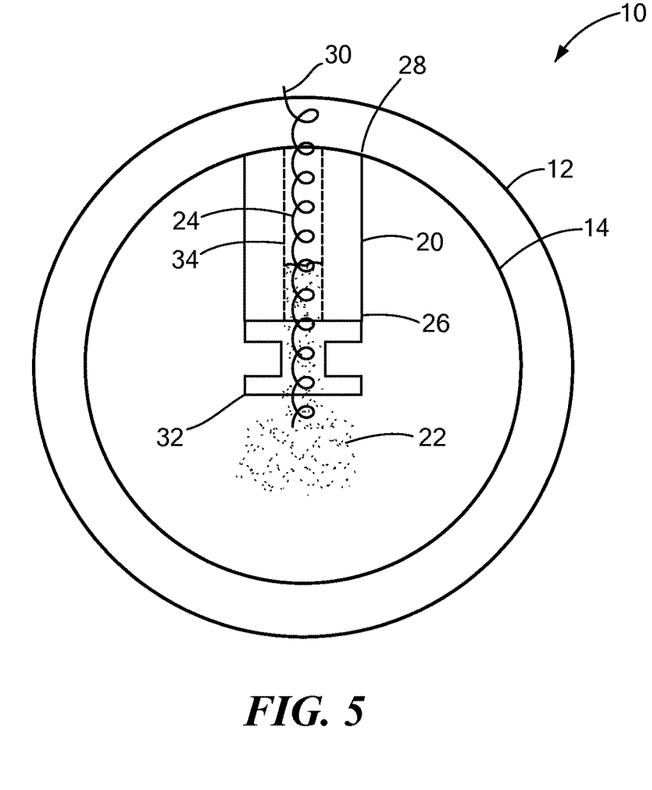
FIG. 5 is a cross-sectional view of another embodiment of the temporary gastric device shown in FIG. 3 showing the separation element punctured.

Referring now to FIG. 5, in an exemplary operation the composition 22 may be injected within the pouch 20 and/or the tube 34, wherein both the pouch 20 and/or the tube 34 are gas impermeable and are generally inflexible. After the user swallows the device 10, the composition 22 begins to produce, for example, $CO_2$ or $N_2$ gas, owing to the temperature increase in the stomach, or through normal chemical reactions occurring within the composition 22, or both. The increase in temperature further causes the piercing element 24 to expand towards the separation element 32 and gradually pierce it, allowing the gases released from the composition 22 to expand and fill the first volume filling agent 14. Alternatively, the piercing element 24 may be composed of an electro-active polymer, similar the second volume filling agent 16, such that it may be activated remotely to expand or release a chemical that punctures the separation element 32.

It is further contemplated that the piercing element 24 may only slightly puncture the separation element 32, such that gases are slowly released into the first volume filling agent 14. For example, after a predetermined time, for example, 180 days, all of the gases may leak out into the first volume filling agent 14, allowing the first volume filling agent 14 to remain expanded for this predetermined period of time. After this predetermined time, the first volume filling agent 14 may degrade, which then harmlessly releases the gases into the stomach. Further, the first volume filling agent 14 and/or pouch 20 may be composed of materials that are resistant to being pierced by the piercing element 24, such that gases are released into the first volume filling agent 14 and not into the stomach through the pouch 20 or first volume filling agent 14 as a result of being pierced. However, the pouch 20 and the first volume filling agent 14 may be fabricated such that the second engagement element 30 extends outward from their respective surfaces without causing a release of gas.

The device 10 may alternatively removed from or inserted into the stomach by an endoscope using an esophageal probe (not shown). For example, the device 10, with or without the delivery structure 10, may be compressed by endoscope or similar device and inserted into the stomach. Once inserted, and the device removed, the device 10 may be allowed to expand to its predetermined biased size. To remove the device 10, the esophageal probe may grasp the first engagement element 18 (FIG. 1A) or the second engagement element 30 (FIG. 5) and transport the device 10 through 10 the esophagus and out the mouth should such a procedure be necessary or desired. Alternatively, the device 10 may be re-sized by using the endoscope to compress the first volume filling agent 14 so that it may be passed through the digestive system.

Figure 6:
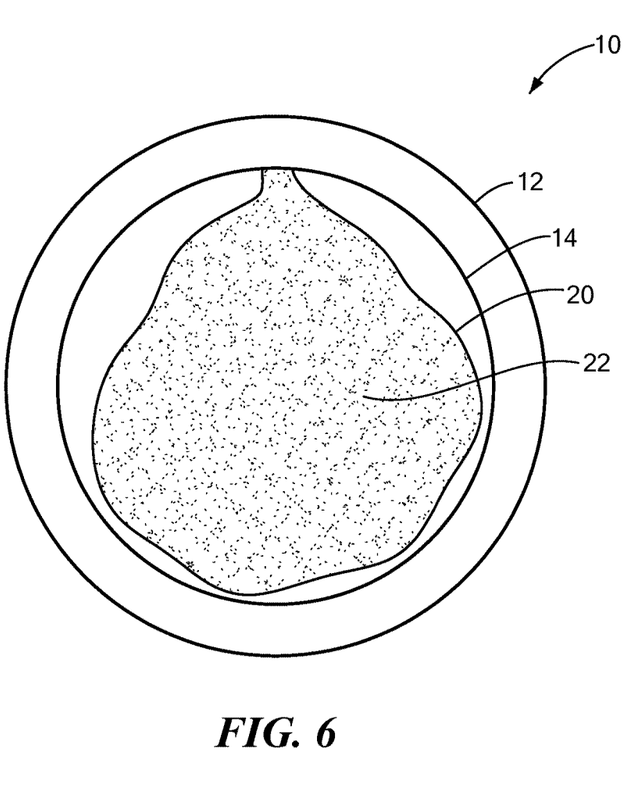
FIG. 6 is a cross-sectional view of another embodiment a temporary gastric device along slice A-A shown in FIG. 1.

Referring now to FIG. 6, in another exemplary operation, the composition 22 may be injected within the pouch 20, the tube 34, or both, in which both the pouch 20 and the tube 34 are gas impermeable and are generally flexible. After the user swallows the device 10, the composition 22 begins to produce, for example, $CO_2$ or $N_2$ gas, owing to the temperature increase in the stomach, or through normal chemical reactions occurring within the composition 22, or both. The pressure exerted by the gases released by the composition 22 exert pressure on the tube 34 and/or pouch 20 causing one or the other or both to expand to expert pressure on and expand the first volume filling agent 14. A sufficient dose of composition 22 may further be injected within the pouch 20 and/or tube 34 such that sufficient gases having sufficient pressure are released for a desired amount of time. After all the gas has been produced, the first volume filling agent 14, the pouch 20 and/or the tube 34 may degrade, and the gases may be harmlessly released into the stomach.

Figure 7:
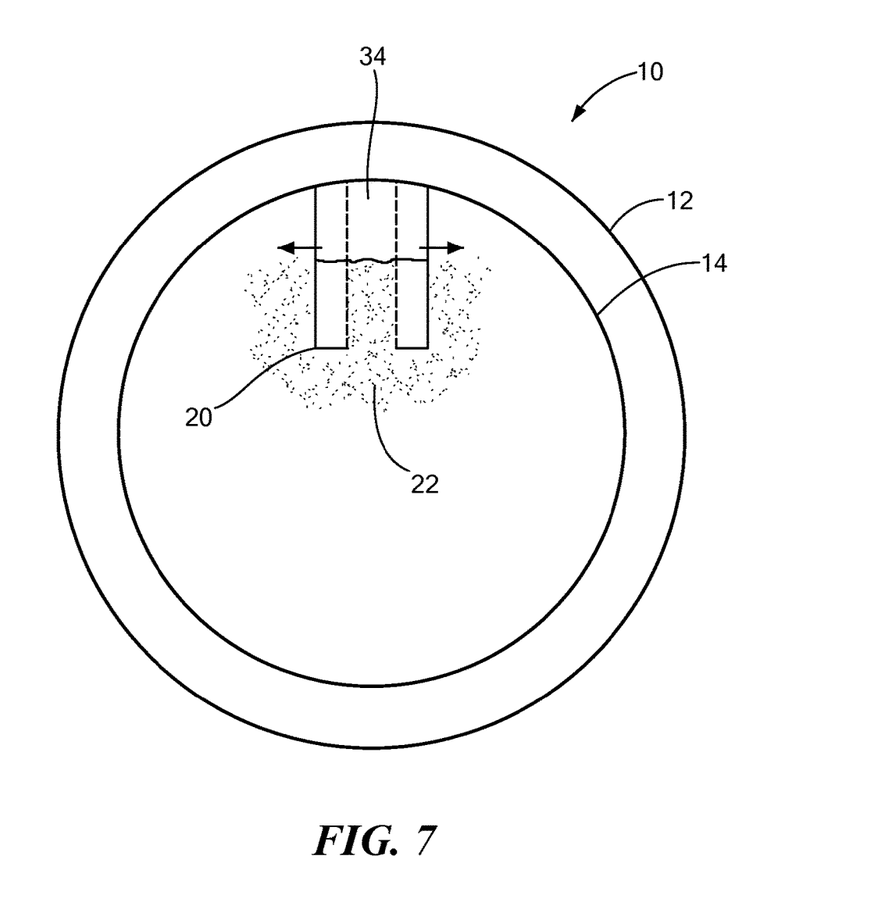
FIG. 7 is a cross-sectional view of another embodiment of the temporary gastric device shown in FIG. 3.

Referring now to FIG. 7, in another embodiment, the composition 22 may be injected with the pouch 20, the tube 34, or both, in which both the pouch 20 and the tube 34 are gas permeable and generally inflexible. The degree of permeability may vary depending on the desired flux of gases out of the pouch 20 and tube 34 in the first volume filling agent 14. For example, the pouch 20 and/or tube 34 may define a porosity such that gases such as $CO_2$ or $N_2$ may diffuse at a desired rate, i.e. the holes defined by the pouch 20 and/or tube 34 may be sized to control the flux of the gases into the first volume filling agent 14. After a predetermined time, for example, 180 days, all the gases may diffuse out of the pouch 20 and/or tube 34. The first volume filling agent 14 may then degrade, be resized or collapsed by an endoscope, and/or pass through the digestive system.

Figure 8:
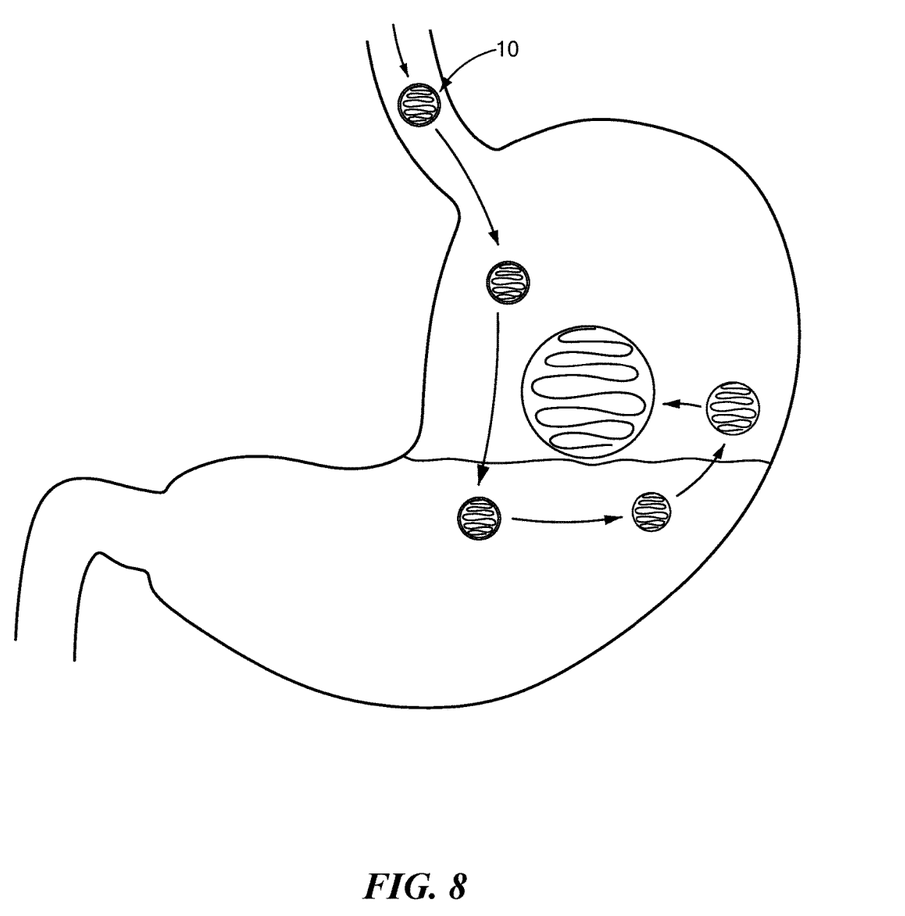
FIG. 8 is a cross-sectional view of a human stomach showing the expansion of an exemplary temporary gastric device.

Referring now to FIG. 8, in each of the above embodiments, the device 10 is configured so that it floats within the stomach when expanded. For example, when food or other contents are disposed within the stomach, the device 10 has sufficient buoyancy to float on top of the stomach contents, owing to the first volume filling agent 14 being filled with gas or having a sufficient low density to float in the stomach. If the stomach is empty, the device 10 has a sufficient size so that it does not occlude the stomach at the junction with the esophagus or the junction with the small intestine or the pyloric valve. As the exact mechanism by which the feeling of satiety is achieved, it is contemplated that the device 10 is operable to reduce the available volume for food in the stomach by partially filling it and/or provides pressure and or/contact to the walls of the stomach to simulate the presence of food.

In an exemplary operation, one or more devices 10 may be swallowed and traverse the esophagus toward the stomach. The device 10 may include a gelatin delivery structure 12 that resists digestive acids and enzymes present in the esophagus and mouth to prevent inadvertent expansion of the device 10. When the device is disposed within the stomach, stomach acid digests the gelatin delivery structure 12 exposing the first volume filling agent 14. The first volume filling agent 14 and/or the second volume filling agent 16 may then transition from a first displacement to a second displacement larger than the first displacement and float atop the stomach contents. After a predetermined time, or through the use an esophageal device, the device 10 may shrink, as discussed above, and pass through the digestive system.

Figure 9:
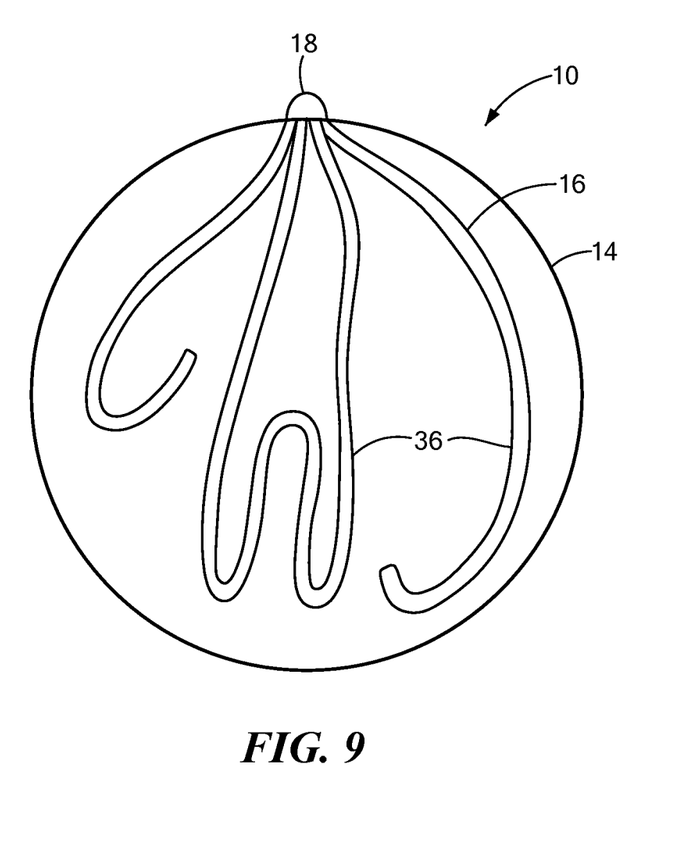
FIG. 9 is a cross-sectional view of another embodiment a temporary gastric device along slice A-A shown in FIG. 1.

Referring now to FIG. 9, the first volume filling agent 14 or the second volume filling agent 16 may be comprised of or include an EAP film that may be wirelessly activated and expanded within the stomach. For example, the first volume filling agent 14 or the second volume filling agent 16 may define a plurality of petals 36, of any shape or size, that expand or cause the expansion of the first volume filling agent 14 or the second volume filling agent 16 to fill a predefined space within the stomach. In an exemplary embodiment, the first volume filling agent 14 or the second volume filling agent 16 may define four petals 36 that radially extend outward from central structure, such as the first engagement element 18. The petals 36 may expand upon wireless activation, which may include energizing or magnetizing the petals 36 such that they expand in response to an applied voltage or current. After a predetermined amount of a time, the petals 36 may be deactivated by wirelessly deenergizing them such that they compress within the device 10 may pass through the digestive system.

Figure 10:
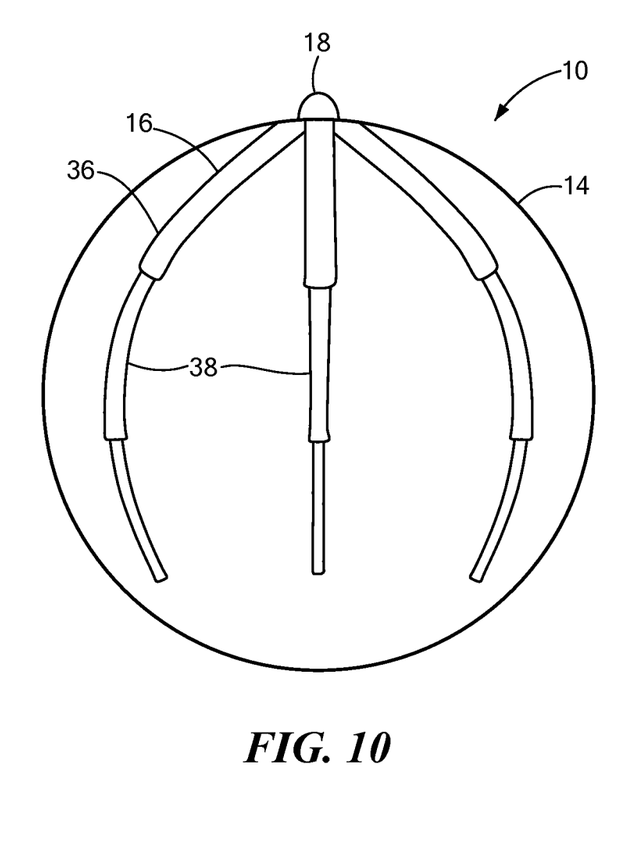
FIG. 10 is a cross-sectional view of another embodiment a temporary gastric device along slice A-A shown in FIG. 9.

Referring now to FIG. 10, the petals 36 may alternatively define a telescoping structure comprised of or including an EAP film than expands from a compressed stated to an expanded state. For example, the petals 36 may define a plurality of sections 38, and upon expansion, each successive section 38 has a small diameter than the previous section 38. This facilitates the nesting of sections 38 within a section 38 that has a larger diameter. Similar to the embodiment shown in FIG. 9, the telescoping petals 36 may be activated wirelessly by passing a current or voltage through the EAP film. The current or voltage can be applied such that a desired number of sections 38 expand or are compressed. For example, each petal 36 may include four sections 38. Upon application of a specified voltage or current, the sections 38 may extend a predetermined distance from a central structure, such as the first engagement element 18. Upon disengagement of the current or voltage, the telescoping sections 38 may retract within each other such that the device 10 is small enough to pass through the digestive track.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A gastric device for a stomach having a pyloric valve comprising:
    a delivery structure housing an ingestible, biodegradable, impermeable polymer balloon with an expandable spherical coil retained therein in a first displacement for delivery;
    the delivery structure being configured to be swallowed and traverse the esophagus to deliver and release the biodegradable, impermeable polymer balloon within the stomach and biodegradable, impermeable polymer balloon being configured to transition from the first displacement to a second displacement larger than the first displacement once released by the delivery structure, the biodegradable, impermeable polymer balloon is configured to not pass through the pyloric valve in the normal digestive process;
    the expandable spherical coil being configured to transition from the first spherical coil displacement to a second spherical coil displacement larger than the first spherical coil displacement after an application of heat, the coil having a first end forming a first engagement element configured to facilitate the retrieval of the device, the first engagement element extending through a wall of the biodegradable, impermeable polymer balloon.

2. The temporary gastric device of claim 1, wherein the biodegradable impermeable polymer balloon is configured to not pass through the pyloric valve in the normal digestive process for at least 30 days.

3. The temporary gastric device of claim 1, wherein the delivery structure is a gelatin capsule.

4. A gastric device for a stomach having a pyloric valve and an esophagus comprising:
    an ingestible delivery structure being configured to be swallowed and traverse the esophagus into the stomach, the delivery structure being composed of a material that degrades upon exposure to stomach acid,
    the delivery structure housing a biodegradable, impermeable polymer balloon and an expandable spherical coil retained within the biodegradable, impermeable polymer balloon in a first displacement,
    the biodegradable, impermeable polymer balloon and expandable spherical coil being configured to transition after an application of heat from the first spherical coil displacement to a second spherical coil displacement larger than the first spherical coil displacement after the delivery structure degrades such that the expandable spherical coil is larger than a diameter of the pyloric valve and is configured to not pass through the pyloric valve,
    the coil having a first end forming a first engagement element configured to facilitate the retrieval of the device, the first engagement element extending through a wall of the biodegradable impermeable polymer balloon.

5. The temporary gastric device of claim 4, wherein the biodegradable, impermeable polymer balloon is composed of a material that degrades upon exposure to stomach acid.

6. The temporary gastric device of claim 5, wherein the expandable spherical coil is composed of a material that degrades upon exposure to stomach acid soon after the biodegradable impermeable polymer balloon degrades.

7. The temporary gastric device of claim 5, wherein the expandable spherical coil is composed of a material that degrades after a predetermined amount of time or in response to a solvent, acid, or other chemical that may be ingested following the predetermined amount of time.

8. The temporary gastric device of claim 5, wherein a surface of the expandable spherical coil is coated with a pharmaceutical or antimicrobial agent that is eluded from the surface.

9. The temporary gastric device of claim 4, wherein the expandable spherical coil is composed of an electroactive polymer such that it can be expanded and/or contracted remotely and may be re-sized over time for adjustment and/or for removal.

10. The temporary gastric device of claim 4, wherein the expandable spherical coil includes sensors or actuators configured to respond to an applied electric field, magnetic or electromagnetic, to adjust a size of the expandable spherical coil.

* * * * *